– –
United States Patent [19]

Feeney

[11] Patent Number: 5,390,534

[45] Date of Patent: Feb. 21, 1995

[54] IMPACT TESTING DEVICE

[75] Inventor: Brian P. Feeney, Enfield, Conn.

[73] Assignee: Lisco, Inc., Tampa, Fla.

[21] Appl. No.: 60,194

[22] Filed: May 7, 1993

[51] Int. Cl.[6] ............................................. G01N 3/00
[52] U.S. Cl. ........................................ 73/79; 73/12.14
[58] Field of Search ................. 73/12.01, 12.02, 12.04,
73/12.06, 12.14, 11.01, 78, 79, 866

[56] References Cited

U.S. PATENT DOCUMENTS

| | | | |
|---|---|---|---|
| 1,240,416 | 9/1917 | Buckwalter | 73/12.14 |
| 1,984,904 | 12/1934 | Warshaw et al. | |
| 2,022,666 | 12/1935 | Haskell et al. | |
| 2,359,044 | 9/1944 | MacBride | 73/12.14 |
| 2,388,246 | 11/1945 | Berger | |
| 2,396,620 | 3/1946 | Taxwood | 73/12.14 |
| 2,476,297 | 7/1949 | Harris | |
| 2,506,607 | 5/1950 | McKendry | 73/11.01 |
| 3,083,564 | 4/1963 | Carter | |
| 3,157,046 | 11/1964 | Orner | 73/12.14 |
| 3,566,668 | 3/1971 | Browning et al. | |
| 3,855,842 | 12/1974 | Imabori et al. | |
| 4,523,759 | 6/1985 | Igarashi | 73/11.01 |

Primary Examiner—Herbert Goldstein
Assistant Examiner—R. Biegel

[57] ABSTRACT

Apparatus to test for the impact strength of a game racket comprising a base plate having an upper surface; a support post extending upwardly from the upper surface of the base plate; a pivot arm having a first end and a second end with clamping components adjacent to the first end adapted to releasably secure the racket to be tested with at least a portion thereof extending beyond the first end; a pivot pin rotatably coupling the second end of the pivot arm to the support post adjacent to its upper end; a pointer coupled to the second end of the pivot arm; an indicator plate with indicia thereon cooperable with the pointer to indicate the angle of the pointer, pivot arm and racket supported thereon with respect to the vertical; and an impact place secured to the upper surface of the base plate, the impact plate having a striking surface with a central extent at a location to be in point contact with the frame of a racket to be tested when supported by the swing arm when in a vertical orientation whereby the swing arm and racket may be pivoted away from the impact plate and released to determine the impact strength of the racket and frame.

6 Claims, 3 Drawing Sheets

IMPACT TESTING DEVICE

BACKGROUND OF THE INVENTION

1. Field of the Invention

This invention relates to an impact testing device and, more particularly, to an apparatus for determining the impact strength of a racket, clamped to a pivot arm, which moves into contact with a fixed, variably positionable, impact plate.

2. Description of the Background Art

There are a series of standard destructive tests within the tennis industry that have been established to evaluate the durability of a composite tennis racket. Each manufacturer may specify different criteria or levels for each test, but will typically use each test in the qualification and inspection of production rackets. These test will normally involve a fatigue test, a horizontal and vertical crush test, and a drop test. The test level required for a racket will be set based on the designer's experience rather than basing it on some correlation between the test and an equivalent force load level experienced during play.

The only impact type test that is typically performed on tennis rackets is called a head drop test. The head drop test involves dropping a racket strung at a specified string tension from a given height on the head of a racket. A standard set-up attaches approximately a 400 gram clamp to the butt of a racket, raises the racket via a string attached to the clamp to a specified height as measured from the lowest point of the racket, and drops the racket on its head. The racket is then inspected for cracks. The requirement for passage of a racket may involve a single or multiple drops from a predetermined height without cracks in the frame. Most likely because impact with a rigid object, i.e., the court, is rather uncommon in tennis, this test seems to be able to adequately predict whether a tennis racket will fail due to impact with the court.

In a racquetball or squash game, impact between the racket and the court, whether floor, side walls or back wall, are much more common and must be taken into account in devising a racket that meets the durability requirements of each game. Impact between the wall and the racket may occur over the entire top half of the head of a racket. The head drop test alone does not sufficiently predict the relative impact strength of a racket for these games. This is probably because the impact point at the top of the head of a racket (12 o'clock position) and the applied load decreases rapidly as you move away from this point. A new test was needed to test the relative impact strength of a racket over the entire top half of the racket.

The present design is similar to an Izod impact test, in that it involves measuring the maximum angle at which a swing arm can be raised and released freely without breaking a particular object, in this case a racket. In the Izod test the test specimen is secured on a fixed support at the bottom of the arc of the swing arm. In the racket impact fixture of the present invention, the racket is attached to the swing arm and impacts against a rigid plate. The plate can be oriented at different angles to vary the location of the impact between the racket and the plate. Through trial and error it was determined that clamping of both the racket handle and the string bed of the racket provided the best correlation to actual impact strength of a racket.

The strength of a particular racket can most readily be established by comparing the angle at which it fails to that of another racket. The relationship between the angle of that swing arm was raised and the energy involved in the subsequent impact is not linear. A calculation of the energy involved in the impact can also be made so that a more quantitative comparison can be made. The calculation involves determining the total weight of the swing arm including the racket (M), finding the location of the center of gravity (Cg), determining the radial distance (R) between the pivot point and the Cg, and calculating the location or height (H) of the Cg at the point form which the swing arm will be released. Assuming no friction in the bearing at the pivot point, then the impact energy (E) will be equal to the potential energy of the swing arm and racket before it is released (E=MGH). The height of the Cg is related to the angle of the swing arm (theta) by the formula H=R+R×sin (theta) ×tan (theta) for angles less than 90 degrees and H=R+R×tan (theta-90) for angles greater than 90 degrees.

For simplicity, impact testing has been limited to impacts with the impact plate at a vertical position and at a 45 degree angle. All rackets tested to this point have failed at lower energies (angles) with the plate at the 45 degree angle, than with the plate at the 90 degree angle. Therefore, the majority of testing has been performed with the plate in this position. Impact of the racket with the plate occurs roughly at the 10 or 2 o'clock positions with the plate fixed at 45 degrees. This is also the most common position in which rackets fail during actual play. Thus far rackets with constructions that fail at higher impact energies in the impact fixture also are failing less in actual play.

Although many types of impact testing devices are known and are in wide use today throughout various industries, none provides the benefits of the present invention. Typical examples of impact testing are described in the patent literature. Note for example, U.S. Pat. Nos. 1,984,904 to Warshaw; 2,022,666 to Haskell; 2,388,246 to Berger; 2,476,297 to Harris; and 3,083,586 to Carter. Each of these patents relate to an impact testing device wherein the object to be tested is fixedly positioned and a moving arm moves into contact therewith at a predetermined speed.

Note is also taken of U.S. Pat. No. 3,566,668 to Browning which relates to an impact testing of an article on a swing arm but has no variable positionable fixed surface to be contacted. Lastly, U.S. Pat. No. 3,885,842 to Imabori describes an impact testing device where a swing arm supports a golf club for testing the dynamic performance of the club.

No prior impact testing device, however, has the capability as does the present invention by utilizing 3T25 swing arm to pilot a racket into contact with fixed, variably positioned plate, for determining the impact strength of the racket.

Accordingly, it is an object of the present invention to provide an apparatus to test for the impact strength of a game racket comprising a base plate having an upper surface; a support post extending upwardly from the upper surface of the base plate; a pivot arm having a first end and a second end with clamping components adjacent to the first end adapted to releasably secure the racket to be tested with at least a portion thereof extending beyond the first end; a pivot pin rotatably coupling the second end of the pivot arm to the support post adjacent to its upper end; a pointer coupled to the second end of the pivot arm; an indicator plate with indicia thereon cooperable with the pointer to indicate the angle of the pointer, pivot arm and racket supported thereon with respect to the vertical; and an impact place secured to the upper surface of the base plate, the impact plate having a striking surface with a central extent at a location to be in point contact with the frame of a racket to be tested when supported by the swing arm when in a vertical orientation whereby the swing arm and racket may be pivoted away from the impact plate and released to determine the impact strength of the racket and frame.

It is a further object of the present invention to swing an object to be tested into contact with a fixed surface for determining the impact strength of the object.

It is a further object of the present invention to vary the angular position of planar surface into which an object to be tested for impact strength is swung.

It is a further object of the present invention to measure the angle at which an object secured to a swing arm is pivoted in order to determine the maximum angle at which an object can be swung prior to breaking.

These objects should be construed to be merely illustrative of some of the more prominent features and applications of the intended invention. Many other beneficial results can be obtained by applying the disclosed invention in a different manner or by modifying the invention within the scope of the disclosure. Accordingly, other objects and a more comprehensive understanding of the invention may be obtained by referring to the summary of the invention, and the detailed description of the preferred embodiment in addition to the scope of the invention defined by the claims taken in conjunction with the accompanying drawings.

SUMMARY OF THE INVENTION

The invention is defined by the appended claims with the specific embodiment shown in the attached drawings. For the purposes of summarizing the invention, the invention may be incorporated into an apparatus to test for the impact strength at which the frame of a composite game racket will break, the composite game racket being of the type having a frame of a composite material shaped centrally into a string-holding loop at the head end and with the ends of the frame in a close side by side relationship for being held by a player at the handle end, the apparatus comprising a base plate positionable on a support surface, the base plate having a horizontal upper surface; an elongated, fixedly positioned, essentially vertically disposed, support post extending upwardly from the upper surface of the base plate, the support post having a centrally disposed longitudinal axis extending along the length thereof; an elongated pivot arm having a first and a second end, clamping components on the pivot arm adjacent to the first end for releasable securement of the handle of a game racket to be tested with at least a portion of the head extending beyond the first end; an elongated clamping mechanism releasably secured to the pivot arm adjacent to the first end, the clamping mechanism adapted to contact and secure the strings of the racket to be tested; a pivot pin rotatably coupling the second end of the pivot arm with respect to the support post adjacent to its upper end for allowing a swinging motion of the pivot arm with respect to the support post about a first horizontal axis in a plane of rotation, the pivot pin having a diameter coextensive with the longitudinal centerlines of the support post and the pivot arm; an elongation pointer coupled to the second end of the pivot arm, the pointer having a longitudinal axis coextensive with the axis of the swing arm; an indicator plate with indicia thereon cooperable with the pointer to indicate the angle of the pointer, pivot arm and racket supported thereon to be tested with respect to the vertical centerline of the support post; and an impact plate rotatably secured to the upper surface of the base plate, the impact plate having a striking surface positionable perpendicular to the plane of rotation of the swing arm and with a central extent at a location to be in point contact with the frame of a racket to be tested when supported by the swing arm when in a vertical orientation, the impact plate being adjustably positionable between a plurality of positions to vary the point on the racket frame which contacts the impact plate when the swing arm and racket are pivoted away from the impact plate and released to determine the angle of release where breakage of the racket frame occurs to thereby determine the impact strength of the racket and frame.

The invention may also be incorporated into an apparatus to test for the impact strength of a game racket comprising a base plate having an upper surface; a support post extending upwardly from the upper surface of the base plate; a pivot arm having a first end and a second end with clamping components adjacent to the first end adapted to releasably secure the racket to be tested with at least a portion thereof extending beyond the first end; a pivot pin rotatably coupling the second end of the pivot arm to the support post adjacent to its upper end; a pointer coupled to the second end of the pivot arm; an indicator plate with indicia thereon cooperable with the pointer to indicate the angle of the pointer, pivot arm and racket supported thereon with respect to the vertical; and an impact place secured to the upper surface of the base plate, the impact plate having a striking surface with a central extent at a location to be in point contact with the frame of a racket to be tested when supported by the swing arm when in a vertical orientation whereby the swing arm and racket may be pivoted away from the impact plate and released to determine the impact strength of the racket and frame.

The apparatus further includes an elongated clamping mechanism releasably secured to the pivot arm adjacent to the first end, the clamping mechanism adapted to contact and secure the strings of the racket to be tested. The apparatus further includes means to adjustably position the impact plate between a plurality of positions to vary the point of the racket frame which contacts the impact plate when the swing arm and racket are pivoted away from the impact plate and released to determine the angle of release where breakage of the racket frame occurs to thereby determine the impact strength of the racket and frame. The pivot arm has a plurality of apertures along the length thereof and the apparatus further includes a plurality of brackets and bolts operatively associated with preselected apertures to allow for the variable positioning of the racket to be tested on the pivot arm. The apparatus further includes weight means attachable to the pivot arm to vary the impact energy from a given drop angle.

The foregoing has outlined rather broadly, the more pertinent and important features of the present invention. The detailed description of the invention that follows is offered so that the present contribution to the art may be more fully appreciated. Additional features of the invention will be described hereinafter. These form the subject of the claims of the invention. It should be appreciated by those skilled in the art that the conception and the disclosed specific embodiment may be readily utilized as a basis for modifying or designing other methods and structures for carrying out the same purposes of the present invention. It should also be realized by those skilled in the art that such equivalent methods and structures do not depart from the spirit and scope of the invention as set forth in the appended claims.

BRIEF DESCRIPTION OF THE DRAWINGS

For a more succinct understanding of the nature and objects of the invention, reference should be directed to the following description taken in conjunction with the accompanying drawings in which.

Similar reference numerals refer to similar parts throughout the several Figures.

DETAILED DESCRIPTION OF THE PREFERRED EMBODIMENT OF THE INVENTION

Figure 1:
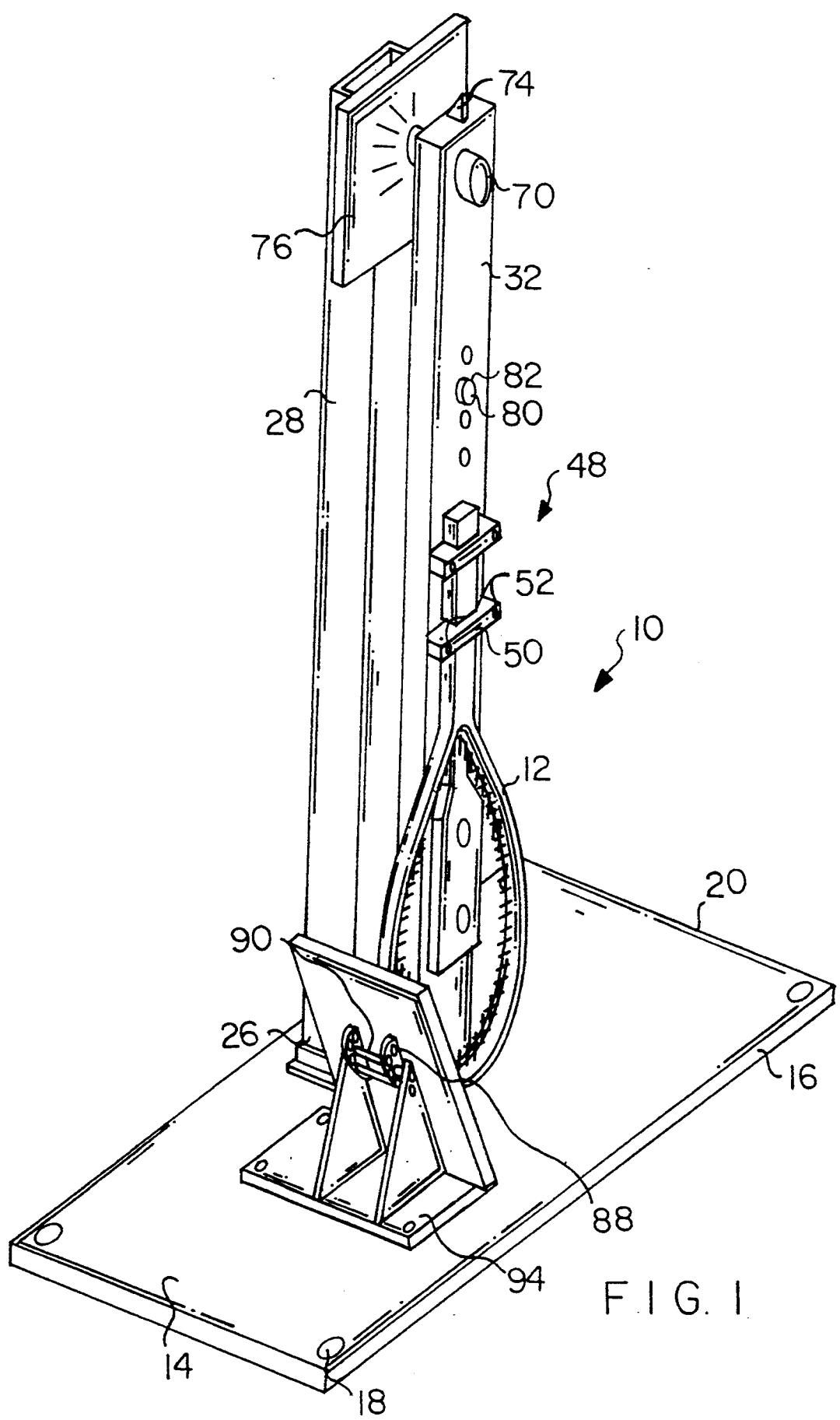
FIG. 1 is a perspective illustration of an impact testing device constructed in accordance with the principles of the present invention.
Figure 2:
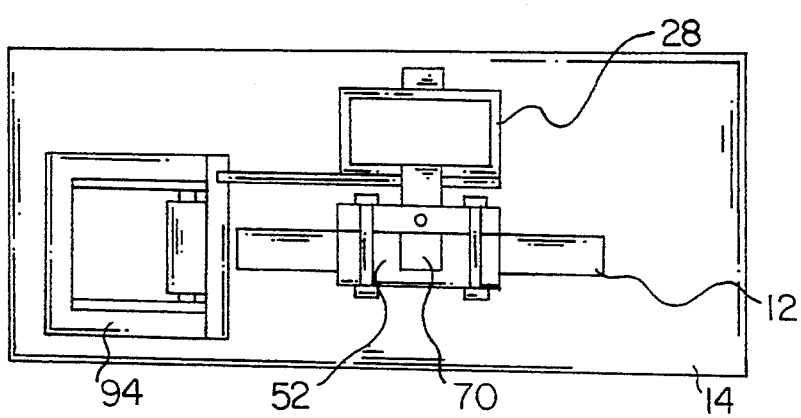
FIGS. 2 and 3 are a plan and front elevational view of the impact testing device of FIG. 1 showing the pivot arm in an alternate position.
Figure 3:
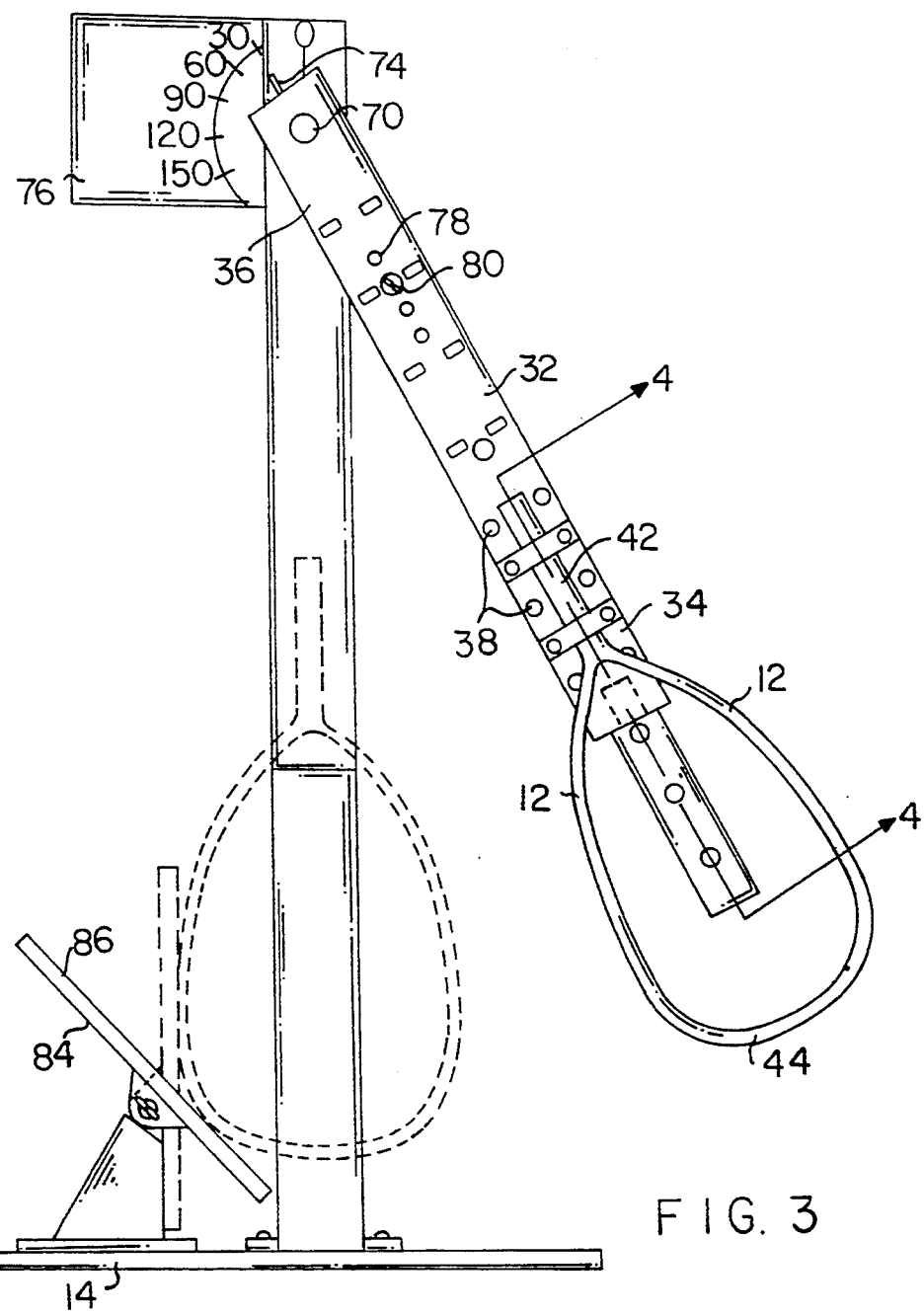

The apparatus of the present invention is an impact strength testing device 10 and is best seen in FIG. 1. The testing device is adapted to support a game racket 12, whether a tennis racket, squash racket, badminton racket, racquet ball racket or the like in contact with a fixed but variably positionable surface in order to determine the angle or energy at which the racket may be swung without breaking in order to determine the impact strength of the racket.

The testing device includes a rigid base plate 14 preferably of a heavy metallic material such as cast iron. Its lower surface 16 is adapted to be supported on the upper surface of a test table or the like. Holes 18 in its corners allow for permanent coupling to a suitable surface. It also has an upper support surface 20 for receipt of the operative mechanisms of the device. The upper horizontal surface 20 has centrally positioned thereon the lower end 26 of an elongated fixably positioned support post 28, preferably formed as a hollow tubular metallic member. The support post 28 is mounted in an essentially vertical disposition extending upwardly from the upper surface of the base plate. The centrally disposed longitudinal axis extends along the length thereof in a vertical orientation.

The second major component of the device is a pivot arm 32. The pivot arm is an elongated member having a central elongated axis along its length. It has a first or lower end 34 and a second or upper end 36. Apertures 38 are formed along the length of the pivot arm near its edges adjacent to the lower end. These are used for releasably securement of a handle 42 of the game racket to be tested. It is preferred that at least a portion of the end of the racket remote from the handle, the head end 44 extend downwardly beyond the first end 34 of the swing arm 32.

Clamping mechanisms 48 includes a pair of plates 50 with four corner holes associated bolts 52 and nuts 54 function to clamp the racket in its extended orientation for testing.

Figure 4:
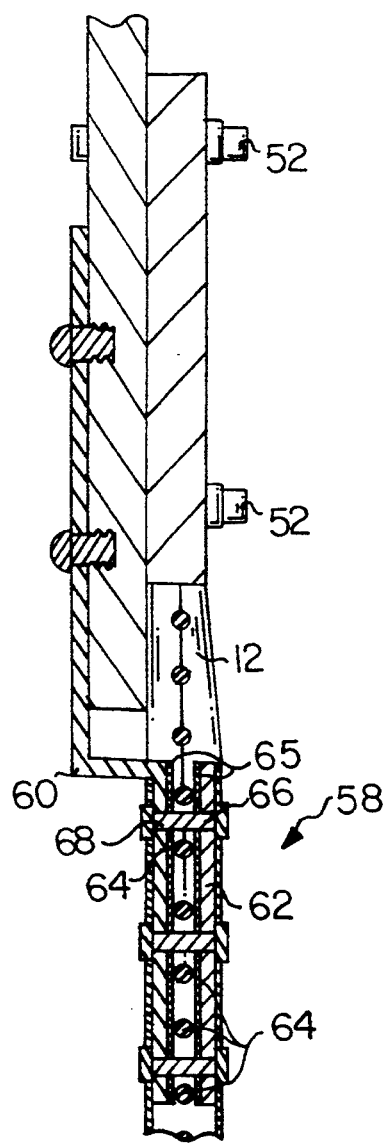
FIG. 4 is a sectional view taken along lines 4—4 of FIG. 3.
Figure 5:
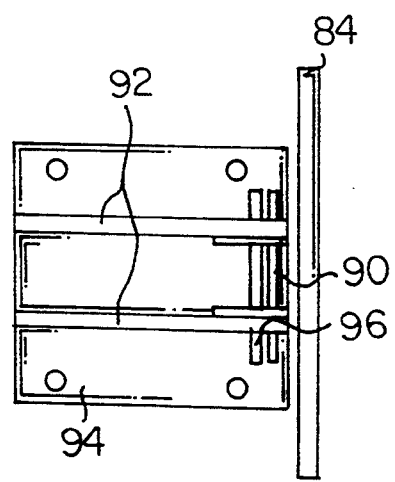
FIGS. 5 and 6 are a plan and side elevational view of the impact plate and associated components.
Figure 6:
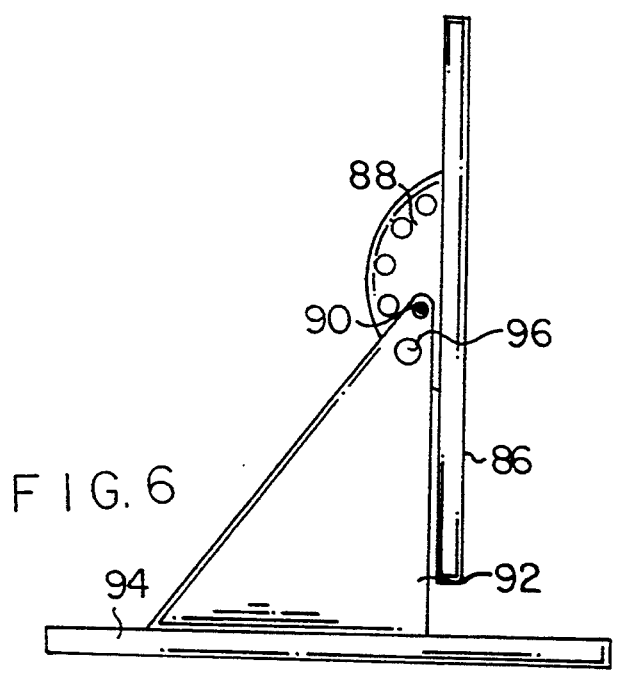

Additional clamping mechanisms 58 also extend downwardly from the first end of the pivot arm. Note FIG. 4. These clamping mechanisms include a pair of planar plates 60 and 62 with surfaces in contact with the strings 64 of the racket to be tested. The upper end of the interior clamping mechanisms is formed with appropriate bends to render it releasably couplable to the lower end of the pivot arm. Bolts 66 in threaded apertures 68 effect such coupling. The mating plates 60 and 62 are secured thereover with the string bed of the racket therebetween. The facing surfaces of the plates are preferably provided with elastomeric surfaces 64 to preclude damage to the strings.

The pivot arm is rotatably coupled to the support post through a pivot pin. The pivot pin 70 has a central horizontal access through the centerlines of the support post and swing arm. The pivot pin allows for full rotational motion of the pivot arm with respect to the support post. The pivot pin by its central orientation has a diameter coextensive with the longitudinal centerlines of the support post and the pivot arm when the pivot arm is depending downwardly in a vertical orientation.

Adjacent to the upper or second end of the swing arm is an elongated pointer 74. The pointer comes to a point and has a central axis coextensive with the central axis of the swing arm with which it moves in an oscillatory manner. In association with the pointer is an indicator plate 76 with indicia thereon. When the swing arm is pivoted, the pointer will rotate to point to the indicia on the indicator plate to indicate the angle at which the pivot arm is located. Such angle is measured from the vertical centerline of the support post.

The pivot arm 32 is also provided with a series of holes 78 in a central extent thereof. In this manner any of a plurality of weights 80 may be removably secured to the pivot arm to vary its weight selectively so that the speed of the rotating pivot arm and racket may be varied to thereby vary the impact force for a particular drop angle. A wing nut and bolt 82 secure the weight in position.

The last component of the apparatus is an impact plate 86. The impact plate is secured to the base plate 14. The impact plate is rotatably secured thereto and has a striking surface 86 of a hard and rigid construction. The impact plate and the striking surface are positionable perpendicular to the planar rotation of the swing arm. The central extent of the striking surface is at a location to be in point contact with the frame of the racket being tested when supported by a swing arm and the swing arm is in its vertically extending orientation.

The impact plate is provided with a clevice 88 and rod 90 which is cooperable with upstanding arms 92, attached to the base plate 14 through an intermediate plate 92. The rod 90, extending through holes in the clevice and arms, allows pivoting of the pivot plate to adjustably vary the position of the striking surface between a plurality of orientations. This allows a tester to vary the point on the racket at which the frame will contact the impact plate.

An adjustment pin 96 is removably positionable through holes in the arms 92 and preselected holes in the clevice 88 to hold the impact plate and its striking surface in a preselected orientation.

The swing arm and racket are pivoted away from the impact plate by lifting. When released, the racket strikes the impact plate to determine the impact strength of the racket frame. To determine the angle of release, it is simply measured between the pointer and indicia plate 98 to determine the angle where breakage of the racket and frame occur. This determines the impact strength of the invention.

The present disclosure includes that contained in the appended claims as well as that of the foregoing description. Although this invention has been described in its preferred form with a certain degree of particularity, it should be understood that the present disclosure of the preferred form has been made only by way of example and that numerous changes in the details of construction and combination and arrangement of parts may be resorted to without departing from the spirit and scope of the invention.

Now that the invention has been described,
What is claimed is:

1. Apparatus to test for the impact strength at which the frame of a composite game racket will break, the composite game racket being of the type having a frame of a composite material shaped centrally into a string-holding loop at the head end and with the ends of the frame in a close side relationship for being held by a player at the handle end, the apparatus comprising:

a base plate positionable on a horizontal support surface, the base plate having a horizontal upper surface;

an elongated, fixedly positioned, essentially vertically disposed, support post extending upwardly from the upper surface of the base plate, the support post having a centrally disposed longitudinal vertical centerline extending along the length thereof;

an elongated pivot arm having a lower first end and an upper second end and a longitudinal centerline therebetween, clamping components on the pivot arm adjacent to the first end for releasable securement of the handle of a game racket to be tested with at least a portion of the head extending downwardly beyond the first end;

an elongated clamping mechanism releasably secured to the pivot arm adjacent to the first end, the clamping mechanism being adapted to contact and secure the strings of the racket to be tested;

a horizontal pivot pin rotatably coupling the second end of the pivot arm with respect to the support post adjacent to its upper end for allowing a swinging motion of the pivot arm with respect to the support post about a first horizontal axis in a vertical plane of rotation, the pivot pin having a diameter coextensive with the longitudinal centerlines of the support post and the pivot arm;

an elongated pointer coupled to the second end of the pivot arm, the pointer having a longitudinal axis coextensive with the axis of the pivot arm;

an indicator plate with indicia thereon cooperable with the pointer to indicate the angle of the pointer, pivot arm and racket supported thereon to be tested with respect to the vertical centerline of the support post; and an impact plate rotatably secured to the upper surface of the base plate, the impact plate having a striking surface positionable perpendicular to the plane of rotation of the swing arm and with a central extent at a location to be in point contact with the frame of a racket to be tested when supported by the swing arm when in a vertical orientation, the impact plate being adjustably positionable between a plurality of angular positions with respect to the vertical to vary the point on the racket frame which contacts the impact plate when the swing arm and racket are pivoted away from the impact plate and released to determine the angle of release where breakage of the racket frame occurs to thereby determine the impact strength of the racket and frame.

2. Apparatus to test for the impact strength of a game racket comprising:

a base plate having a horizontal upper surface;

a vertical support post extending upwardly from the upper surface of the base plate;

a pivot arm having a lower first end and an upper second end with clamping components adjacent to the first end adapted to releasably secure the racket to be tested with at least a portion thereof extending downwardly beyond the first end;

a horizontal pivot pin rotatably coupling the second end of the pivot arm to the support post adjacent to its upper end;

a pointer coupled to the second end of the pivot arm;

an indicator plate with indicia thereon cooperable with the pointer to indicate the angle of the pointer, pivot arm and racket supported thereon with respect to the vertical; and an impact plate secured to the upper surface of the base plate, the impact plate having a striking surface in a plane offset from the vertical with a central extent at a location to be in point contact with the frame of a racket to be tested when supported by the swing arm when in a vertical orientation whereby the swing arm and racket may be pivoted away from the impact plate and released to determine the impact strength of the racket and frame.

3. The apparatus as set forth in claim 2 and further including an elongated clamping mechanism releasably secured to the pivot arm adjacent to the first end, the clamping mechanism being adapted to contact and secure the strings of the racket to be tested.

4. The apparatus as set forth in claim 2 and further including means to adjustably position the impact plate between a plurality of angular positions with respect to the vertical to vary the point of the racket frame which contacts the impact plate when the swing arm and racket are pivoted away from the impact plate and released to determine the angle of release where breakage of the racket frame occurs to thereby determine the impact strength of the racket and frame.

5. The apparatus as set forth in claim 2 wherein the pivot arm has a plurality of apertures along the length thereof and further including a plurality of brackets and bolts operatively associated with preselected apertures to allow for the variable positioning of the racket to be tested along the centerline of the pivot arm.

6. The apparatus as set forth in claim 2 and further including at least one weight attachable to the pivot arm to vary the impact energy from a given drop angle.

* * * * *